US006331540B1

(12) United States Patent
Kabra

(10) Patent No.: US 6,331,540 B1
(45) Date of Patent: Dec. 18, 2001

(54) PHARMACEUTICAL COMPOSITIONS CONTAINING A FLUOROQUINOLONE ANTIBIOTIC DRUG AND XANTHAN GUM

(75) Inventor: Bhagwati P. Kabra, Arlington, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/686,083

(22) Filed: Oct. 10, 2000

Related U.S. Application Data
(60) Provisional application No. 60/162,693, filed on Nov. 1, 1999.

(51) Int. Cl.$^7$ .................. A61K 31/535; A61K 47/00; A61K 33/14

(52) U.S. Cl. .............. 514/230.2; 514/780; 514/782; 514/235.5; 514/947; 424/675; 424/678

(58) Field of Search .................. 514/230.2, 782, 514/780, 235.5, 250, 912, 947; 424/402, 59, 493, 678, 675

(56) References Cited

U.S. PATENT DOCUMENTS

| | | | |
|---|---|---|---|
| 3,700,451 | 10/1972 | Sullivan, Jr. | 96/66 |
| 3,784,712 | 1/1974 | Glicksman et al. | 426/167 |
| 3,944,427 | 3/1976 | Sullivan, Jr. | 106/208 |
| 4,135,979 | 1/1979 | Corley et al. | 195/31 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,638,059 | 1/1987 | Sutherland | 536/121 |
| 4,647,470 | 3/1987 | Sanderson et al. | 426/573 |
| 4,661,475 | 4/1987 | Bayerlein et al. | 514/54 |
| 4,708,861 | 11/1987 | Popescu et al. | 424/1.1 |
| 4,717,713 | 1/1988 | Zatz et al. | 514/2 |
| 4,775,632 | 10/1988 | Gozard et al. | 435/104 |
| 4,861,760 | 8/1989 | Mazuel et al. | 514/54 |
| 4,996,197 | 2/1991 | Mazuel | 514/54 |
| 5,192,535 | 3/1993 | Davis et al. | 424/78.04 |
| 5,212,162 | 5/1993 | Missel et al. | 514/54 |
| 5,234,957 | 8/1993 | Mantelle | 514/772.6 |
| 5,318,780 | 6/1994 | Viegas et al. | 424/427 |
| 5,403,841 | 4/1995 | Lang et al. | 514/226.8 |
| 5,422,116 | 6/1995 | Yen et al. | 424/427 |
| 5,446,070 | 8/1995 | Mantelle | 514/772.6 |
| 5,461,081 | 10/1995 | Ali et al. | 514/772.3 |
| 5,462,749 | 10/1995 | Rencher | 424/484 |
| 5,473,062 | 12/1995 | Haze et al. | 536/114 |
| 5,493,015 | 2/1996 | Murofushi et al. | 536/127 |
| 5,587,175 | 12/1996 | Viegas et al. | 424/427 |
| 5,610,184 | 3/1997 | Shahinian, Jr. | 514/540 |
| 5,618,800 | 4/1997 | Kabra et al. | 514/57 |
| 5,679,336 | 10/1997 | Ali et al. | 424/78.04 |
| 5,736,161 | * 4/1998 | Garces et al. | 424/493 |
| 5,759,563 | 6/1998 | Yewey et al. | 424/426 |
| 5,888,493 | 3/1999 | Sawaya | 424/78.04 |
| 6,153,208 | * 11/2000 | McAtee et al. | 424/402 |
| 6,166,012 | * 12/2000 | Muller et al. | 514/235.5 |

FOREIGN PATENT DOCUMENTS

| | | |
|---|---|---|
| 1070629 | 1/1980 | (CA) . |
| 0 331 617 A1 | 9/1989 | (EP) . |
| 0 374 658 A2 | 12/1989 | (EP) . |
| 0 410 326 A2 | 7/1990 | (EP) . |
| 0 424 043 A1 | 10/1990 | (EP) . |
| 0 424 043 B1 | 5/1993 | (EP) . |
| 0 780 121 A1 | 12/1996 | (EP) . |
| 96/03990 | 2/1996 | (WO) . |
| 98/11874 | 3/1998 | (WO) . |
| 98/17249 | 4/1998 | (WO) . |
| 98/41171 | 9/1998 | (WO) . |
| 98/53809 | 12/1998 | (WO) . |
| 99/00133 | 1/1999 | (WO) . |
| 99/51273 | 10/1999 | (WO) . |

OTHER PUBLICATIONS

Carrington et al., "Polyelectrolyte Behaviour of Dilute Xanthan Solutions: Salt Effects on Extensional Rheology," Polymer, vol. 37 (13); pp. 2871–2875 (1996).

Foss et al., "Thermal Stability and Chain Conformational Studies of Xanthan at Different Ionic Strenghts," Carbohydrate Polymer, vol. 7, pp. 421–433 (1987).

Gamini et al., "Physico–chemical Properties of Aqueous Solutions of Xanthan: An n.m.r. Study," Carbohydrate Research, vol. 220, pp. 33–47 (1991).

Kelco Product Brochure, "Xanthan Gum—Natural Biogum for Scientific Water Control," Fifth Edition (1994).

Kierulf et al., "Thermal Stability of Xanthan Preparations," Carbohydrate Polymers, vol. 9, pp. 185–194 (1988).

Lambert et al., "On the Thermal Stability of Xanthan Gum," Polymer, vol. 26, pp. 1549–1553 (1985).

Lund et al., Properties of Xanthan Solutions after Long-–Term Heat Treatment at 90°C, Polymer Degradation and Stability, vol. 27, pp. 211–225 (1990).

McNeely et al., Industrial Gums, Academic Press, Inc., San Diego, CA, (1973), Chapter VII. "Xanthan Gum," pp. 486–497.

Meseguer et al., "Gamma Scintigraphic Comparison of Eyedrops Containing Pilocarpine in Healthy Volunteers," J. of Ocular Pharmacology and Therapeutics, vol. 12(4), pp. 481–488 (1996).

Meseguer et al., "Gamma Scintigraphic Study of Precorneal Drainage and Assessment of Miotic Response in Rabbits of Various Ophthalmic Formulations Containing Pilocarpine," International J. of Pharmaceutics, vol. 95, pp. 229–234 (1993).

Milas et al., "The Effect of Thermal Aging on Xanthan Solutions," J. of Applied Polymer Science, vol. 35, pp. 1115–1122 (1988).

(List continued on next page.)

Primary Examiner—Zohreh Fay
Assistant Examiner—Brian-Yong Kwon
(74) Attorney, Agent, or Firm—Patrick M. Ryan

(57) ABSTRACT

Pharmaceutical compositions containing a fluoroquinolone antibiotic drug, xanthan gum and a water-soluble calcium salt in an amount sufficient to make the fluoroquinolone antibiotic drug and xanthan gum compatible are disclosed.

7 Claims, No Drawings

OTHER PUBLICATIONS

Nolte et al., "Gelation of Xanthan With Trivalent Metal Ions," *Carbohydrate Polymers* vol. 18 (4), pp. 243–251 (1992).

Oviatt et al., "Thermal Treatment of Semi–dilute Aqueous Xanthan Solutions Yields Weak Gels with Properties Resembling Hyaluronic Acid," *Int. J. Biol. Macromol.*, vol. 15(3), pp. 3–10.

Sanford et al., "Microbial Polysaccharides: New Products and Their Commerical Applications," *Pure & Appl. Chem.*, vol. 56(7), pp. 879–892 (1984).

Shatwell et al., "The Influence of Acetyl and Pyruvate Substitutents on the Helix—Coil Transition Behaviour or Xanthan," Carbohydrate Research, vol. 206 (1), pp. 87–103 (1990).

Smith et al., "Influence of the Pyruvate Content of Xanthan on Macromolecular Association in Solution," *Int. J. Biol. Macromol.*, vol. 3, pp. 129–134 (1981).

Tait et al., "Acid Hydrolysis and High–Performance Liquid Chromatography of Xanthan," *Carbohydrate Polymers*, vol. 13, pp. 133–148 (1990).

* cited by examiner

PHARMACEUTICAL COMPOSITIONS CONTAINING A FLUOROQUINOLONE ANTIBIOTIC DRUG AND XANTHAN GUM

This application claims priority to co-pending U.S. Provisional Application, U.S. Serial No. 60/162,693, filed Nov. 1, 1999.

BACKGROUND OF THE INVENTION

1. Field of the Invention

The present invention relates to pharmaceutical compositions. In particular, this invention relates to pharmaceutical compositions formulated so that fluoroquinolone antibiotic drugs and xanthan gum are compatible.

2. Description of Related Art

Xanthan gum is a polysaccharide known to be useful in ophthalmic compositions as a viscosity-enhancing agent. U.S. Pat. No. 4,136,177 discloses ophthalmic compositions containing an ophthalmic drug and from about 0.01 to 2.5% (w/v) of xanthan gum. The '177 patent teaches that if the concentration of xanthan gum is from about 0.02 to about 1.0% (w/v), the composition is suitable for "dropwise" ophthalmic applications. In contrast, at concentrations of xanthan gum above about 1.0% and up to about 2.5% (w/v), "a gel-like consistency is attained." Thus, the '177 patent discloses compositions that are formulated to be either non-gelled liquids or gels before instillation in the eye. The '177 patent does not describe any xanthan gum-containing compositions as capable of being administered as a liquid and gelling upon contact with the eye. According to the '177 patent, any ophthalmic drug can be added to the xanthan gum-containing compositions, but the '177 patent does not include a fluoroquinolone antibiotic drug when it lists suitable antibacterial drugs (see Col. 3, lines 54–58).

WO 99/51273 discloses gel-forming compositions containing xanthan gum where the xanthan gum has an initial bound acetate content of at least about 4% and an initial bound pyruvate content of at least about 2.5%. The entire contents of WO 99/51273 are hereby incorporated by reference.

Ciprofloxacin is an antibiotic drug known to be useful in pharmaceutical compositions. Because of solubility limitations, topically administrable aqueous compositions containing 0.3% (w/w) ciprofloxacin are generally formulated at low pH (e.g., pH 4.5) in order to avoid ciprofloxacin precipitating out of the composition. U.S. Pat. No. 5,679,336 discloses topically administrable pharmaceutical compositions formulated as solutions at or near physiological pH using polystyrene sulfonic acid.

Adding 0.3% (w/w) ciprofloxacin to a simple aqueous xanthan gum-containing composition, even at a pH of 4.5, causes a precipitate to form between ciprofloxacin and xanthan gum.

SUMMARY OF THE INVENTION

The present invention is directed toward a method of making fluoroquinolone antibiotic drugs and xanthan gum compatible in aqueous pharmaceutical compositions. According to the present method, a calcium salt is added to the composition in an amount sufficient to make the fluoroquinolone drug compatible with xanthan gum. The present invention is also directed toward compositions containing a fluoroquinolone drug, xanthan gum and a calcium salt in an amount sufficient to make the fluoroquinolone drug and xanthan gum compatible. The methods and compositions of the present invention include a minimum of 0.15 wt. % of calcium salt such that the formulations have a turbidity rating of $\leq 40$ NTU (nephelos turbidity units) at room temperature.

Among other factors, the present invention is based upon the finding that, unlike salts of monovalent cations or multivalent anions, calcium salts are particularly effective in making ciprofloxacin and xanthan gum compatible in pharmaceutical compositions.

DETAILED DESCRIPTION OF THE INVENTION

Unless otherwise indicated, all ingredient concentrations are listed as % (w/w).

Xanthan gum is a well-known polysaccharide that is commercially available from a variety of sources. The amount of xanthan gum contained in the compositions of the present invention will depend upon the properties desired for the final composition and the identity and concentration of other ingredients in the composition, but will generally range from about 0.4 to about 0.8%, preferably 0.5 –0.7%.

Xanthan gum is generally available in at least two grades from some commercial suppliers, a food or industrial grade and a pharmaceutical grade. It is preferable to polish filter even pharmaceutical grade materials so that the finished pharmaceutical product will have increased clarity. As one skilled in the art appreciates, the appropriate filter size for polish filtration depends upon the size of the undesired impurities contained in raw material. For example, in the case of a solution composition, it has been found that the Rhodigel Clear grade of xanthan gum from Rhone- Poulenc Inc. should be filtered through a 0.45 $\mu$m filter in order to remove cell debris and impurities. Multiple stages of filters can be used to increase the overall efficiency of the polish filtration process.

Although the amount of the fluoroquinolone drug included in the compositions of the present invention will be whatever amount is therapeutically effective and will depend upon a number of factors, including the identity and potency of the chosen drug, the total concentration of drug will generally be about 1% or less. A preferred fluoroquinolone antibiotic drug is ciprofloxacin. In topically administrable ophthalmic compositions, the preferred concentration of ciprofloxacin will range from 0.2 –0.4%.

In addition to xanthan gum and a fluoroquinolone antibiotic drug, the compositions of the present invention include a water-soluble calcium salt in an amount sufficient to make the xanthan gum and the fluoroquinolone drug compatible. The necessary amount of calcium salt will depend upon the concentration of xanthan gum, the identity and concentration of the fluoroquinolone drug and the desired clarity of the final formulation. In general, however, the calcium salt concentration should be sufficient to give the final formulation a turbidity (nephelos) rating of $\leq 40$ NTU at room temperature. The calcium salt concentration is preferably ≧0.15%. Suitable water-soluble calcium salts include calcium chloride, calcium lactate; calcium acetate; calcium propionate and calcium ascorbate. The most preferred calcium salt is calcium chloride.

The compositions of the present invention may include other components. For example, the compositions may include a second active agent (not limited to anti-infective agents). The compositions may also contain one or more excipients including, but not limited to, pharmaceutically acceptable buffering agents, preservatives (including preservative adjuncts), tonicity-adjusting agents including salts containing monovalent cations, surfactants, solubilizing agents, stabilizing agents, comfort-enhancing agents, emollients, pH-adjusting agents and/or lubricants.

The following examples are presented to illustrate further various aspects of the present invention, but are not intended to limit the scope of the invention in any respect.

EXAMPLES

Each of the formulations shown in Tables 1–3 below was prepared as follows. If present, benzododecinium bromide (BDAB), acetic acid, sodium acetate and edetate disodium were combined with purified water, followed by the indicated salt(s) and then, if present, ciprofloxacin. All ingredients were dissolved by stirring and pH was adjusted, if necessary. Then xanthan gum stock solution was added and the resulting formulation mixed by stirring to give a homogeneous composition. If necessary, pH was adjusted again. The resulting formulation was then autoclaved at 121° C. for 30 minutes (using liquid cycle). The sterilized formulations were then cooled to room temperature and added to a test tube.

Viscosity at 1.2, 6, and in some cases 120 $s^{-1}$, was measured for certain samples using a Brookfield Rheometer. Visual appearance or turbidity was recorded for each sample. Turbidity (NTU) was measured at room temperature using a DRT-100B turbidimeter (H. F. Scientific). The results appear in Tables 1–3 immediately below the list of ingredients for each formulation.

Example 1

Monovalent Cations

TABLE 1

| | % (w/w) | | | | | | | |
|---|---|---|---|---|---|---|---|---|
| Ingredient | A | B | C | D | E | F | G | H |
| Ciprofloxacin HCl Monohydrate | 0.35 | 0.35 | 0.35 | 0.35 | 0.35 | 0.35 | 0.35 | 0.35 |
| Xanthan Gum | 0.6 | 0.6 | 0.6 | 0.6 | 0.6 | 0.3 | 0.3 | 0.6 |
| Mannitol | 0 | 0 | 0 | 0 | 4.6 | 4.6 | 0 | 0 |
| Potassium Chloride | 1.1 | 0 | 0 | 0 | 0 | 0 | 0 | 0 |
| Sodium Chloride | 0 | 0.86 | 0.86 | 0.66 | 0 | 0 | 0.86 | 0.86 |
| Calcium Chloride Dihydrate | 0 | 0 | 0 | 0 | 0 | 0 | 0 | 0 |
| Boric Acid | 0 | 0 | 0 | 0.4 | 0 | 0 | 0 | 0 |
| Polysorbate 80 | 0 | 0 | 0.05 | 0 | 0 | 0 | 0 | 0 |
| Edetate Disodium | 0.05 | 0.05 | 0.05 | 0.05 | 0.05 | 0.05 | 0.05 | 0.05 |
| Acetic acid | 0.04 | 0.04 | 0.04 | 0.04 | 0.04 | 0.04 | 0.04 | 0.04 |
| Sodium acetate | 0.03 | 0.03 | 0.03 | 0.03 | 0.03 | 0.03 | 0.03 | 0.03 |
| BDAB | 0.012 | 0.012 | 0.012 | 0.012 | 0.012 | 0.012 | 0.012 | 0.012 |
| NaOH/HCl | pH 4.5 | pH 4.5 | pH 4.5 | pH 4.5 | pH 4.5 | pH 4.5 | pH 4.5 | pH 4.5 |
| Purified Water | qs | qs | qs | qs | qs | qs | qs | qs |
| Turbidity (NTU) | 68 | 67 | 49 | 74 | 248 | 793 | 36 | 70 |
| Viscosity at 1.2 $s^{-1}$ | 3300 | 3100 | — | 3100 | Gel | 200 | 280 | 3030 |
| Viscosity at 6 $s^{-1}$ | 1040 | 1000 | — | 980 | Clumps | 45 | 170 | 980 |

Example 2

Multivalent Anions

TABLE 2

| | % (w/w) | | | | |
|---|---|---|---|---|---|
| Ingredient | I | J | K | L | M |
| Ciprofloxacin HCl Monohydrate | 0.35 | 0.35 | 0 | 0.35 | 0 |
| Xanthan Gum | 0.6 | 0.6 | 0.6 | 0.3 | 0.3 |
| Sodium Sulfate | 1.5 | 1.5 | 1.5 | 1.5 | 1.5 |
| Edetate Disodium | 0.05 | 0.05 | 0.05 | 0.05 | 0.05 |
| Polysorbate 80 | 0.05 | 0.05 | 0.05 | 0.05 | 0.05 |
| BDAB | 0.012 | 0.012 | 0.012 | 0.012 | 0.012 |
| NaOH/HCl | pH 4.5 | pH 6.6 | pH 4.5 | pH 4.5 | pH 4.5 |
| Purified Water | qs | qs | qs | qs | qs |
| Appearance | Almost Clear | Precipitate | Clear | Clear | Clear |
| Viscosity at 1.2 $s^{-1}$ | 2700 | — | 4700 | 640 | 690 |
| Viscosity at 6 $s^{-1}$ | 830 | — | 1300 | 280 | 300 |
| Viscosity at 120 $s^{-1}$ | 76 | — | 106 | 37 | 38 |

In each of Formulations I, J and L, small particles were observed after the formulations were left standing for one week.

Example 3

Multivalent Cations

TABLE 3

| Ingredient | % (w/w) | | | | |
|---|---|---|---|---|---|
| | N | O | P | Q | R |
| Ciprofloxacin HCl Monohydrate | 0.35 | 0.35 | 0 | 0.35 | 0 |
| Xanthan Gum | 0.6 | 0.6 | 0.6 | 0.3. | 0.3 |
| Calcium Chloride Dihydrate | 1.2 | 1.2 | 1.2 | 1.2 | 1.2 |
| Edetate Disodium | 0.05 | 0.05 | 0.05 | 0.05 | 0.05 |
| Polysorbate 80 | 0.05 | 0.05 | 0.05 | 0.05 | 0.05 |
| BDAB | 0.012 | 0.012 | 0.012 | 0.012 | 0.012 |
| NaOH/HCl | pH 4.5 | pH 6.6 | pH 4.5 | pH 4.5 | pH 4.5 |
| Purified Water | qs | qs | qs | qs | qs |
| Appearance | Clear | Hazy | Clear | Clear | Clear |
| Viscosity at 1.2 s$^{-1}$ | 4800 | 5300 | 4800 | 1130 | 1340 |
| Viscosity at 6 s$^{-1}$ | 1230 | 1350 | 1230 | 370 | 390 |
| Viscosity at 120 s$^{-1}$ | 95 | 103 | 95 | 37 | 38 |

| Ingredient | S | T | U | V | W | X | Y | Z |
|---|---|---|---|---|---|---|---|---|
| Ciprofloxacin HCl Monohydrate | 0.35 | 0.35 | 0.35 | 0.35 | 0.35 | 0.35 | 0.35 | 0.35 |
| Xanthan Gum | 0.6 | 0.6 | 0.6 | 0.6 | 0.6 | 0.6 | 0.6 | 0.6 |
| Sodium Chloride | 0 | 0 | 0.45 | 0 | 0.26 | 0 | 0 | 0 |
| Calcium Chloride Dihydrate | 1.4 | 1.3 | 0.7 | 1.1 | 0.7 | 1.1 | 0.7 | 1.4 |
| Boric Acid | 0 | 0 | 0 | 0.4 | 0.4 | 0.4 | 0.4 | 0 |
| Polysorbate 80 | 0 | 0 | 0 | 0 | 0 | 0.05 | 0.05 | 0 |
| Edetate Disodium | 0.05 | 0.05 | 0.05 | 0.05 | 0.05 | 0.05 | 0.05 | 0.05 |
| Acetic acid | 0.04 | 0.04 | 0.04 | 0.04 | 0.04 | 0.04 | 0.04 | 0.04 |
| Sodium acetate | 0.03 | 0.03 | 0.03 | 0.03 | 0.03 | 0.03 | 0.03 | 0.03 |
| BDAB | 0.012 | 0.012 | 0.012 | 0.012 | 0.012 | 0.012 | 0.012 | 0.012 |
| NaOH/HCl | pH 4.5 | pH 4.5 | pH 4.5 | pH 4.5 | pH 4.5 | pH 4.5 | pH 4.5 | pH 4.5 |
| Purified Water | qs | qs | qs | qs | qs | qs | qs | qs |
| Turbidity (NTU) | 15 | 7 | 15 | 34 | 30 | 29 | 27 | 20 |
| Viscosity at 1.2 s$^{-1}$ | 5600 | — | — | 6000 | 4000 | — | — | 3860 |
| Viscosity at 6 s$^{-1}$ | 1370 | — | — | 1630 | 1140 | — | — | 1130 |

| Ingredient | AA | AB | AC | AD | AE | AF |
|---|---|---|---|---|---|---|
| Ciprofloxacin HCl Monohydrate | 0.35 | 0.35 | 0.35 | 0.35 | 0.35 | 0.35 |
| Xanthan Gum | 0.6 | 0.6 | 0.6 | 0.6 | 0.6 | 0.6 |
| Sodium Chloride | 0.26 | 0.26 | 0.26 | 0.5 | 0.65 | 0.78 |
| Calcium Chloride Dihydrate | 0.7 | 0.7 | 0.7 | 0.5 | 0.3 | 0.1 |
| Boric Acid | 0 | 0.4 | 0.4 | 0 | 0 | 0 |
| Polysorbate 80 | 0 | 0 | 0.05 | 0 | 0 | 0 |
| Edetate Disodium | 0.05 | 0.05 | 0.05 | 0.05 | 0.05 | 0.05 |
| Acetic acid | 0.04 | 0.04 | 0.04 | 0.04 | 0.04 | 0.04 |
| Sodium acetate | 0.03 | 0.03 | 0.03 | 0.03 | 0.03 | 0.03 |
| BDAB | 0.012 | 0.012 | 0.012 | 0.012 | 0.012 | 0.012 |
| NaOH/HCl | pH 4.5 | pH 4.5 | pH 4.5 | pH 4.5 | pH 4.5 | pH 4.5 |
| Purified Water | qs | qs | qs | qs | qs | qs |
| Turbidity (NTU) | 26 | 33 | 25 | 24 | 27 | 43 |
| Viscosity at 1.2 s$^{-1}$ | 4200 | 3670 | 4300 | — | — | — |
| Viscosity at 6 s$^{-1}$ | 1210 | 1070 | 1230 | — | — | — |

Formulations S, T and U were left standing at room temperature for 5 months. All other formulations in Table 3 were left standing at room temperature for at least two weeks. No particulates were observed after these time periods in any of the formulations shown in Table 3.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A method of enhancing the stability of an aqueous pharmaceutical composition containing 0.4 –0.8% (w/w) xanthan gum and a fluoroquinolone antibiotic drug comprising the step of adding to the composition a water-soluble calcium salt in an amount of at least 0.15% (w/w), such that the composition is homogeneous and has a turbidity rating (NTU)≦40 at room temperature.

2. The method of claim 1 wherein the concentration of flucroquinolone antibiotic drug is 1% (w/w) or less.

3. The method of claim 2 wherein the fluoroquinolone antibiotic drug is ciprofloxacin and the concentration of fluoroquinolone antibiotic drug is 0.2 –0.4% (w/w).

4. The method of claim 1 wherein the calcium salt is selected from the group consisting of calcium chloride, calcium lactate; calcium acetate; calcium propionate and calcium ascorbate.

5. The method of claim 4 wherein the calcium salt is calcium chloride.

6. The method of claim 4 wherein the calcium salt is present at a concentration of at least 0.3% (w/w).

7. The method of claim 1 wherein the composition further comprises a water-soluble salt of a monovalent cation.

* * * * *